(12) United States Patent
Hogendoorn et al.

(10) Patent No.: US 10,151,817 B2
(45) Date of Patent: Dec. 11, 2018

(54) FLOWMETER WITH A MEASURING DEVICE IMPLEMENTING A TOMOGRAPHIC MEASURING PRINCIPLE

(71) Applicant: Krohne AG, Basel (CH)

(72) Inventors: Cornelis Johannes Hogendoorn, Sijk (NL); Rutger Reinout Tromp, Dordrecht (NL); Marco Leendert Zoeteweij, Hendrik-Ido-Ambach (NL); Olaf Jean Paul Bousché, Dordrecht (NL)

(73) Assignee: KROHNE AG, Basel (CH)

( * ) Notice: Subject to any disclaimer, the term of this patent is extended or adjusted under 35 U.S.C. 154(b) by 554 days.

(21) Appl. No.: 14/627,206

(22) Filed: Feb. 20, 2015

(65) Prior Publication Data

US 2015/0234026 A1 Aug. 20, 2015

(30) Foreign Application Priority Data

Feb. 20, 2014 (DE) .................. 10 2014 002 224
Jul. 10, 2014 (DE) .................. 10 2014 010 238

(51) Int. Cl.
 *G01R 33/563* (2006.01)
 *G01F 1/58* (2006.01)
 (Continued)

(52) U.S. Cl.
 CPC ............ *G01R 33/563* (2013.01); *G01F 1/58* (2013.01); *G01N 33/18* (2013.01); *G01N 33/28* (2013.01)

(58) Field of Classification Search
 CPC .................................................. G01R 33/563
 See application file for complete search history.

(56) References Cited

U.S. PATENT DOCUMENTS 5,498,960 A * 3/1996 Vinegar ................... G01V 3/32
 324/303
5,936,405 A * 8/1999 Prammer ............. G01N 24/081
 324/303

(Continued)

FOREIGN PATENT DOCUMENTS

WO WO 2009030870 A1 * 3/2009 ............... G01F 1/44

OTHER PUBLICATIONS

Ismail et al, "Tomography for multi-phase flow measurement in the oil industry," Flow Measurement and Instrumentation, vol. 16, issues 2-3, Apr.-Jun. 2005, pp. 145-155, (Published May 2005).*

*Primary Examiner* — Dixomara Vargas
(74) *Attorney, Agent, or Firm* — David S. Safran; Roberts Mlotkowski Safran Cole & Calderon, P.C.

(57) ABSTRACT

A flowmeter for determining the flow of a multi-phase medium through a measuring tube has a first and a second measuring device, one of which operates on a tomographic measuring principle and one of uses a measuring principle based on nuclear magnetic resonance. The first measuring device operates in a different manner from the second measuring device, e.g., using a measuring device operating on the measuring principle of pre-magnetization contrast measurement and having a pre-magnetization section with a constant magnetic field. The magnetic field has at least one component perpendicular to the direction of flow of the multi-phase medium and is generated by using magnetic field generating elements, which are arranged around the measuring tube. Additionally, an assembly for exciting nuclear spin by a RF excitation pulse or a RF excitation pulse sequence is part of the measuring device.

1 Claim, 3 Drawing Sheets

(51) Int. Cl.
*G01N 33/18* (2006.01)
*G01N 33/28* (2006.01)

(56) References Cited

U.S. PATENT DOCUMENTS

| | | | | |
|---|---|---|---|---|
| 6,046,587 A * | 4/2000 | King | ................ | E21B 47/102 324/306 |
| 6,242,912 B1 * | 6/2001 | Prammer | ............ | G01N 24/081 324/303 |
| 6,268,727 B1 * | 7/2001 | King | ................ | E21B 47/102 324/306 |
| 6,512,371 B2 * | 1/2003 | Prammer | ............ | G01N 24/081 324/303 |
| 6,868,906 B1 * | 3/2005 | Vail, III | ............ | E21B 4/04 166/250.01 |
| 6,956,371 B2 * | 10/2005 | Prammer | ............ | G01N 24/081 324/300 |
| 7,013,997 B2 * | 3/2006 | Vail, III | ............ | E21B 7/065 166/386 |
| 7,036,610 B1 * | 5/2006 | Vail, III | ............ | E21B 21/10 175/261 |
| 7,040,420 B2 * | 5/2006 | Vail, III | ............ | E21B 7/065 175/171 |
| 7,075,297 B2 * | 7/2006 | Freedman | ............ | G01N 24/081 324/303 |
| 7,100,710 B2 * | 9/2006 | Vail, III | ............ | E21B 7/065 166/386 |
| 7,108,084 B2 * | 9/2006 | Vail, III | ............ | E21B 7/065 175/257 |
| 7,147,068 B2 * | 12/2006 | Vail, III | ............ | E21B 7/065 175/65 |
| 7,196,517 B2 * | 3/2007 | Freedman | ............ | G01N 24/081 324/303 |
| 7,234,542 B2 * | 6/2007 | Vail, III | ............ | E21B 7/065 175/261 |
| 7,698,954 B2 * | 4/2010 | Tombs | ............ | G01F 1/74 73/861.356 |
| 7,768,260 B2 * | 8/2010 | Chen | ............ | G01N 24/081 324/303 |
| 8,165,817 B2 * | 4/2012 | Betancourt | ............ | G01V 11/00 702/13 |
| 9,133,709 B2 * | 9/2015 | Huh | ............ | E21B 47/1015 |
| 9,551,769 B2 * | 1/2017 | Fordham | ............ | G01R 33/4818 |
| 2008/0174309 A1 * | 7/2008 | Pusiol | ............ | G01F 1/56 324/306 |
| 2013/0144548 A1 * | 6/2013 | Xie | ............ | G01R 27/00 702/65 |

\* cited by examiner

FLOWMETER WITH A MEASURING DEVICE IMPLEMENTING A TOMOGRAPHIC MEASURING PRINCIPLE

BACKGROUND OF THE INVENTION

Field of the Invention

The invention relates to a flowmeter for determining the flow of a multiphase medium flowing through a measuring tube having a measuring device implementing a tomographic measuring principle. The invention also relates to a method for operating such a flowmeter.

Description of Related Art

The atomic nuclei of the elements that have nuclear spin also have a magnetic moment caused by the nuclear spin. The nuclear spin can be regarded as angular momentum describable by a vector and correspondingly, the magnetic moment can also be described by a vector, which is oriented parallel to the vector of the angular momentum. If a macroscopic magnetic field is present, the vector of the magnetic moment of the atomic nucleus tends to orient itself parallel to the vector of the macroscopic magnetic field at the atomic nucleus. Here, the vector of the magnetic moment of the atomic nucleus precesses around the vector of the macroscopic magnetic field at the atomic nucleus. The frequency of the precession is called Larmor frequency $\omega_L$ and is proportional to the magnitude of the magnetic field strength B. The Larmor frequency is calculated according to $\omega_L = \gamma \cdot B$ where $\gamma$ is the gyromagnetic ratio, which is at a maximum for hydrogen atoms. The gyromagnetic ratio indicates the proportionality factor between the angular momentum or the spin of a particle and the associated magnetic moment.

Measurement and analysis methods that use the properties of precession of atomic nuclei having a magnetic moment when a macroscopic magnetic field is present are called nuclear magnetic resonance measurement or analysis methods. Nuclear magnetic resonance is abbreviated to NMR.

An important representative of the measuring principles is magnetic resonance tomography, also called magnetic resonance imaging, MRI. Normally, electric signals induced by the precessing atomic nuclei under different limiting conditions in a sensor coil are used as output variable for the measurement and analysis method.

An example of measuring devices that use magnetic resonance are nuclear magnetic flowmeters, which measure the flow of a multiphase medium flowing through a measuring tube and analyze the medium.

A requirement for analysis using nuclear magnetic resonance is that the phases of the medium to be analyzed are able to be excited into distinguishable nuclear magnetic resonances. The analysis can include the flow velocity of the individual phases of the medium and the relative fractions of the individual phases in the multiphase medium. Nuclear magnetic flowmeters can, for example, be used for analysis of multiphase mediums extracted from oil sources. The medium then consists essentially of the phases crude oil, natural gas and salt water, wherein all phases contain hydrogen atomic nuclei.

The analysis of the medium extracted from oil sources can also take place using so-called test separators. These channel off a small portion of the extracted medium, separate the individual phases of the medium from one another and determine the fractions of the individual phases in the medium. However, test separators are not able to reliably measure crude oil fractions of less than 5%. Since the crude oil fractions of many sources is already less than 5%, it is not possible at this time to economically exploit these sources using test separators. In order to further economically exploit sources with a very small crude oil fraction, accordingly exact flowmeters are necessary.

Normally, electric signals induced by the precessing atomic nuclei after excitation in a sensor coil are used as output variable for evaluation. A requirement for the measurement of a multi-phase medium is, as already mentioned, that the individual phases of the medium can be excited to distinguishable nuclear magnetic resonances. The magnitude of the electric signals induced by the precessing atomic nuclei of one phase of the medium in the sensor coil is dependent on the number of precessing atomic nuclei per volume element in this phase, thus depending on the density of the phase, but also on the influence time of the precessing atomic nuclei in the influencing, controlled magnetic field. Thus, the magnitude of the induced electric signal in the liquid phases is greater than in the gaseous phases.

Spatial information necessary for magnetic resonance imaging is, for example, applied to the sample with a gradient field. Since the Larmor frequency of the atomic spin is proportional to the magnetic field strength, a location-dependent distribution of different Larmor frequencies of the atomic spins is created by the gradient field and thus a spatial dependency of the electric signals induced by the atomic nuclei.

As described above, the MRI signal is dependent on the density of the medium. In a comparison of the average values of the signal amplitudes per cubic meter of gas, oil and water, it can be determined that the signal from gas is clearly different than that of oil and water, however, there is almost no difference between the signals from oil and water. The strength of the signal can be expressed by the so-called hydrogen index HI. The hydrogen index HI describes the relative fraction of hydrogen atoms of a medium compared to water. Accordingly, the hydrogen index of water $HI_{water}=1$. The indices for oil and gas are $HI_{oil}=0.9-1.1$ and $HI_{gas}=0-0.2$. With the help of the MR signals, it is easy to distinguish gas, on the one hand, and liquid (consisting of water and oil), on the other hand. Differentiating between water and oil is difficult or very complex, since the amplitudes of the MR signals are barely different.

As already described, nuclear magnetic measurement and analysis methods are based on the effect that the magnetic moments of the nucleus are aligned along the field line of an externally applied magnetic field. This leads to a bulk magnetization of the medium. The rate at which this magnetization establishes is determined by the so-called spin lattice relaxation time $T_1$ and has an exponential course.

A further measurement variable typical for nuclear magnetic measurement and analysis methods is the spin-spin relaxation time $T_2$. This time is a measure for inhomogeneity in the magnetic field surrounding the one single spin.

The mechanisms, which determine the values for $T_1$ and $T_2$, are dependent on the molecular dynamics of the test sample. The molecular dynamics are, in turn, dependent on the size of the molecules and also on the intermolecular spacing. These are different for each medium. Accordingly, different mediums also have different values for $T_1$ and $T_2$.

A measurement method known from the prior art for characterizing individual phases of a multi-phase medium is given by the measuring principle of pre-magnetization contrast measurement. This measuring principle is based on the difference in the $T_1$ time for different phases of a multiphase medium and is suitable in a distinct manner for determining the oil fraction and the water fraction as well as the relative ratio of the oil fraction to the water fraction in a sample.

The multiphase medium flows through a section interfused with a constant magnetic field. Here, the magnetic field has at least one component perpendicular to the direction of flow of the medium. Since the alignment of the magnetic moments in the magnetic field is dependent on the respective phase of the medium, different formation of magnetization in the individual phases results at the same exposure time. The exposure time of the magnetic field is determined by the length of the section interfused by the constant magnetic field and the flow velocity of the medium.

In general, the longitudinal relaxation time $T_1$ of oil is much smaller than that of water. Accordingly, the magnetization of oil parallel to the outer magnetic field establishes more quickly than for water. By varying the length of the pre-magnetization section, the signals from oil and water are each formed at a different level, so that the ratio of oil fraction to water fraction in the medium can be determined from the oil-water signal ratio dependent on the pre-magnetization section. The strong contrast between oil signal and water signal depending on the pre-magnetization section offers a good possibility for determining the oil to water ratio (OWR) of the medium.

Since the signal of the gas fraction is very weak, the method is, on the one hand, independent of the gas fraction. However, on the other hand, it is not suitable for determining the gas fraction, so that not all three phases of the medium can be characterized using the measuring principle of pre-magnetization contrast measurement.

Another measuring principle, which is also often used in flow measurement technology and is not based on nuclear spin resonance is by electrical capacitance tomography (ECT).

Electrical capacitance tomography is a method known from the prior art for measuring and characterizing multi-phase media. It is generally suitable for dielectric materials and is based on the fact that different materials have different permittivities.

A typical measuring device for electrical capacitance tomography is designed in such a manner that a certain number of electrodes are arranged around a measuring tube. Measuring devices known from the prior art usually have eight, twelve or sixteen electrodes.

In a measuring device of the type being described, an excitation voltage is applied to an electrode and the induced voltage/the current is measured in all other electrodes, while their electric potential is kept at zero. This is carried out for all existing electrodes. Using the example of a measuring device with eight electrodes, the first electrode is used in a first step as excitation electrode and the second to eighth electrodes are used as detector electrodes. In the next step, the second electrode is used as an excitation electrode and the third through eighth electrodes are used as detector electrodes, etc. In a measuring device with N electrodes, there are $N \cdot (N-1)/2$ electrode pair combinations, and thus, $N \cdot (N-1)/2$ measuring values of capacity from which an image can be constructed. The construction occurs by means of an evaluation algorithm, which is not explained in detail here.

Since the capacity is dependent on the permittivity, i.e., the permeability of a material for an electric field, of the multiphase medium between the electrodes, it is thus possible to dissolve the distribution of the individual phases using the measured values, since each phase of the medium has a different permittivity.

The permittivity of gas is about 1, $\varepsilon_r \approx 1$, the permittivity of oil between 2 and 4, $\varepsilon_r \approx 2-4$, and the permittivity of water is greater than 50, $\varepsilon_r > 50$. Using the values shown here for the permittivity of the individual phases, it can be observed that it is very difficult and complex to separate the gaseous phase from the oil phase, since the values of permittivity characterizing the two phases are not far from one another, namely almost the same. Electrical capacitance tomography was shown above to be a good method for determining the hydrocarbon fraction of a multi-phase medium, which is made up of the oil fraction and the gas fraction, and the water fraction of the medium.

The measuring principles described above, as shown, have great advantages in the measurement of certain properties of a multiphase medium. On the other hand, however, they also have the shown disadvantages or limitations so that the determination of all three phases of the multiphase medium is either not possible, inexact or extremely complex.

SUMMARY OF THE INVENTION

The object of the present invention is thus to provide a flowmeter and a method for operating the flowmeter according to the invention in which all three phases of the multiphase medium can be reliably determined in a simple manner.

The flowmeter according to the invention in which the above described object is met, is initially and essentially characterized in that at least one further measuring device is provided and at least one of the measuring devices implements a measuring principle based on nuclear magnetic resonance. The second measuring device can realize either also a tomographic or even a non-tomographic measuring principle.

An advantage of the flowmeter according to the invention exists, as compared to the flowmeters known from the prior art, in that it is possible to determine all three phases of the multiphase medium without having to separate the individual phases. As a result, the required effort for the determination of the flow of a multiphase medium flowing through a measuring tube is notably reduced.

Different measuring principles have different advantages and disadvantages. In combining of two measuring device in one flowmeter, which implement the different measuring principles, the disadvantages of one measuring principle can be at least partially compensated by the advantages of the other measuring principle, so that optimized measurement results can be achieved with the combined measuring principles.

A preferred design of the flowmeter according to the invention, in which the tomographic measuring principle is realized by magnetic resonance tomography, is additionally characterized in that one measuring device implements the measuring principle of electrical capacitance tomography. Here, both measuring devices are arranged consecutively in the direction of flow around the measuring tube with multiphase medium flowing through it. The first measuring device can be the one that implements the tomographic measuring principle by magnetic resonance tomography, while the second measuring device can be the one that implements the measuring principle by electrical capacitance tomography. A reversed order of the two measuring devices is, however, just as easily possible.

The measuring device realizing the tomographic measuring principle by magnetic resonance tomography consists of a magnetic resonance tomograph, which is arranged around the measuring tube. The magnetic resonance tomograph preferably includes at least one magnetic field generator for a constant magnetic field and one magnetic field generator for a gradient magnetic field, which can be realized preferably by a gradient coil. The gradient field can be superimposed over the constant magnetic field in order to apply position information to the sample. Additionally, the magnetic resonance tomograph preferably also includes a signal coil for generating a RF excitation pulse or a RF pulse sequence for exciting the nuclear spin as well as a detector coil in order to be able to detect the measuring signal generated by the nuclear spin. Here, the signal coil and the detector coil can be realized either as different coils or as one coil.

Without limiting the generality, the flow direction of the medium through the measuring tube is defined as x-direction. By introducing a coordinate system, the x-axis is chosen along the longitudinal axis of the measuring tube. The y-axis is defined as the horizontal axis, the z-axis is defined as the vertical axis.

The magnetic resonance tomograph is now designed in such a manner that spatial information necessary for tomography can be applied in different directions. The spatial information can, for example, be generated by a gradient field of different gradient directions. This is advantageous, in particular, in that the measurement of each character of the medium can be adapted, which allows for a reduction of the measuring effort.

Generating a gradient field along the z-direction is, in particular, suitable when a medium is present in which the liquid phase and the gas phase are "separate", i.e., for example, the liquid phase flows in the lower region of the tube and the gas phase, due to the lower density, flows in the upper region of the tube. For such a medium, it is sufficient to apply spatial information only in the z-direction in order to completely characterize the medium.

If the multiphase medium is such that the gas phase is mixed with the liquid phase over the entire cross-section of the measuring tube, i.e., for example, in the form of gas bubbles in the liquid, spatial information only in the z-direction is not sufficient for characterizing the entire medium. Moreover, it is now necessary to be able to measure each point along the cross-section of the measuring tube. Consequently, it is necessary to apply spatial information both in the z-direction as well as the y-direction. Implementation can be carried out in two different manners. On the one hand, a gradient field can be generated along the z-axis, $G=G_z \cdot e_z$. Directly thereafter, a gradient field along the y-axis can be generated, $G=G_y \cdot e_y$. In this manner, the spatial information is generated and measured along the z-axis in a first step and in a second step, the position information is generated and measured along the y-axis. A combination of the measuring result sets generated in this manner results in a complete image. On the other hand, it is possible to generate a gradient field that has both a gradient along the z-axis as well as a gradient along the y-axis, $G=G_y \cdot e_y + G_z \cdot e_z$. Spatial information is applied directly to the entire cross-section of the measuring tube by such a field.

It is now possible, to encode the position information in different manners with the help of the gradient field.

If the gradient field is already applied before the excitation of the spin system by the excitation pulse, i.e., if the spins are already precessing depending on position at different Larmor frequencies before excitation, a certain part of the spins can be chosen by the pulse width of the excitation pulse, which is then excited. Thus, a selective excitation of the spin system is present and consequently only the selective excited part of the spins emits a measuring signal.

It is also possible to encode the spatial information using a phase shift of the spin. The gradient field is applied between the excitation of the spin system by an excitation pulse and the reading out of the signals generated by the spin system for a certain time interval. The precession frequency is changed depending on the position by the gradient field since, as already mentioned, the Larmor frequency is proportional to the magnetic field strength. If the gradient field is turned off again, the spins precess again at their "old" frequency, however there was a position-dependent change of the phase of the excited spin, this is called phase encoding.

If the spins are excited by an excitation pulse and then a gradient field is applied during reading ("reading gradient field"), this leads to the spin emitting signals with different, position-dependent frequencies during measurement. The measured "frequency mixture" can be decoded using a Fourier transformation. An encoding of spatial information is thus also possible via the frequency, this is called frequency encoding.

The electrical capacitance tomograph provided as further measuring device can be designed in manner as is described above in general for electrical capacitance tomographs, so that it is not necessary to go into detail here.

The electrical capacitance tomograph includes a number of electrodes, which are symmetrically arranged around the measuring tube. The number of electrodes can be arbitrarily chosen. The electrodes are preferably attachable to the outside of the measuring tube. This guarantees that the flow of the medium is not disturbed and influenced by the electrodes. An excitation voltage is applied to one of the electrodes by a measuring unit and the measuring signal of the remaining electrodes is detected. This procedure is repeated as described above for all electrodes and the distribution of permittivities in the sample reconstructed using an algorithm.

Another preferred embodiment of the flowmeter according to the invention in which the tomographic measuring principle is realized by electrical capacitance tomography, is additionally characterized in that one measuring device implements the measuring principle of pre-magnetization contrast measurement. The measuring device implementing the measuring principle of pre-magnetization contrast measurement includes a pre-magnetization section interfused with a constant magnetic field—wherein the magnetic field has at least one component perpendicular to the flowing medium, as well as a unit, with which the nuclear spins can be excited by a RF excitation pulse or a RF excitation pulse sequence and the measuring signal generated by the nuclear spin can be detected.

In order to implement the measuring principle of the pre-magnetization contrast measurement, the pre-magnetization section interfused with the constant magnetic field must be variable in length, which can be realized in different manners.

It is described above, that the invention also relates to a method for operating a flowmeter for determining the flow of a multiphase medium flowing through a measuring tube, wherein a measuring device implementing a tomographic measuring principle is part of the flowmeter.

There are plural possibilities here, wherein it is common to all possibilities that two measuring principles are used and at least one of the measuring principles is a measuring principle based on nuclear spin resonance.

If the tomographic measuring principle is realized by magnetic resonance tomography, then in addition, either the measuring principle of electrical capacitance tomography or the measuring principle of pre-magnetization contrast measurement can be implemented. If the tomographic measuring principle is realized by electrical capacitance tomography, then in addition the measuring principle of pre-magnetization contrast measurement can be implemented.

If the tomographic measuring principle is realized by magnetic resonance tomography and also the measuring principle of electrical capacitance tomography is implemented, it can be proceeded such that the gaseous fraction $\alpha_G$ and the liquid fraction $\alpha_L$, being the sum of the water fraction $\alpha_W$ and the oil fraction $\alpha_O$, $\alpha_L=\alpha_W+\alpha_O$, are measured by means of magnetic resonance tomography, where the spatial information is encoded by selective excitation and/or phase encoding and/or frequency encoding and a gradient magnetic field is applied along the z-axis, $G=G_z\cdot e_z$, or a gradient magnetic field is applied along the y-axis, $G=G_y\cdot e_y$, or a gradient magnetic field is first applied along the z-axis and then along the y-axis and the data records are combined, or a gradient magnetic field is applied simultaneously along the z-axis and the y-axis, $G=G_y\cdot e_y+G_z\cdot e_z$, that the water fraction $\alpha_W$ and the hydrocarbon fraction $\alpha_C$, being the sum of the oil fraction $\alpha_O$ and the gaseous fraction $\alpha_G$, $\alpha_C=\alpha_O+\alpha_G$, are measured by means of electrical capacitance tomography and the water fraction $\alpha_W$ and the hydrocarbon fraction $\alpha_C$ are determined by the distribution of the permittivities or by the distribution of the conductivity of the medium and that the oil fraction $\alpha_O$ is calculated by subtracting the water fraction $\alpha_W$ measured by means of electrical capacitance tomography from the liquid fraction $\alpha_L$ measured by means of magnetic resonance tomography, which is $\alpha_O=\alpha_{L,MR}-\alpha_{W,ECT}$, or that the oil fraction $\alpha_O$ is calculated by subtracting the gaseous fraction $\alpha_G$ measured by means of magnetic resonance tomography from the hydrocarbon fraction $\alpha_C$ measured by means of electrical capacitance tomography, which is $\alpha_O=\alpha_{C,ECT}-\alpha_{G,MR}$.

Using the method described above, it is recommended further to determine the mean conductivity of the medium from the measured values by means of electrical capacitance tomography, to determine the additional load to the RF resonator circuit of the magnetic resonance tomograph due to the mean conductivity of the medium and/or at least of one conducting phase of the multiphase medium and to enhance the RF-power fed in the medium for exciting the nuclear spins, such that the influence of the additional load due to the mean conductivity on the excitation of the nuclear spins is compensated.

Using the method described above, it is further recommended to proceed such that a conductivity map is generated over the cross sectional area of the measuring tube by means of electrical capacitance tomography, that the mean conductivity of the medium is calculated from the conductivity map, and that additionally the local deviations of the conductivity from the mean conductivity of the medium are determined with the conductivity map, that the additional load to the RF resonator circuit of the magnetic resonance tomograph caused by the mean conductivity of the medium is determined, and that additionally the local dampings of the RF field due to the local deviations of the conductivities from the mean conductivity are determined, and that the RF power fed in the medium for exciting the nuclear spins is enhanced such that the influence of the additional load caused by the mean conductivity on the excitation of the nuclear spins is compensated and additionally RF power is fed locally in the medium, such that the influence of the local conductivities deviating from the mean conductivity on the excitation of the nuclear spins is compensated.

If magnetic resonance tomography is realized as the tomographic measuring principle using the method according to the invention, and additionally the measuring principle of pre-magnetization contrast measurement is implemented, a further teaching of the invention is characterized in that the oil fraction $\alpha_O$ and the water fraction $\alpha_W$ are measured by means of pre-magnetization contrast measurement, wherein the pre-magnetization contrast is realized by changing the length of the pre-magnetization section or by varying the measuring positions and that the gaseous fraction $\alpha_G$ is measured by means of magnetic resonance tomography, where the spatial information is encoded by selective excitation and/or phase encoding and/or frequency encoding and a gradient magnetic field is applied along the z-axis, $G=G_z\cdot e_z$, or a gradient magnetic field is applied along the y-axis, $G=G_y\cdot e_y$, or a gradient magnetic field is first applied along the z-axis and then along the y-axis and the measuring result sets are combined, or a gradient magnetic field is applied simultaneously along the z-axis and the y-axis, $G=G_y\cdot e_y+G_z\cdot e_z$.

Another realization of the method according to the invention, where the tomographic measuring principle is realized by magnetic resonance tomography and in addition the measuring principle of pre-magnetization contrast measurement is implemented, is characterized in that the ratio of the oil fraction $\alpha_O$ to the water fraction $\alpha_W$ is determined by means of pre-magnetization contrast measurement (OWR=$\alpha_O/\alpha_W$), wherein the pre-magnetization contrast is realized by changing the length of the pre-magnetization section or by varying the measuring positions, that the liquid fraction $\alpha_L$ and the gaseous fraction $\alpha_G$ are measured by means of magnetic resonance tomography, where the spatial information is encoded by selective excitation and/or phase encoding and/or frequency encoding and a gradient magnetic field is applied along the z-axis, $G=G_z\cdot e_z$, or a gradient magnetic field is applied along the y-axis, $G=G_y\cdot e_y$, or a gradient magnetic field is first applied along the z-axis and then along the y-axis and the measuring result sets are combined, or a gradient magnetic field is applied simultaneously along the z-axis and the y-axis, $G=G_y\cdot e_y+G_z\cdot e_z$ and that the water fraction $\alpha_W$ is calculated from the liquid fraction $\alpha_L$ measured by means of magnetic resonance tomography and the ratio of the oil fraction $\alpha_O$ to the water fraction $\alpha_W$ OWR by means of measuring the pre-magnetization contrast by $\alpha_W=\alpha_{L,MR}/(OWR+1)$.

As explained, the method according to the invention may also deal with the tomographic measuring principle being realized by electrical capacitance tomography and also using the measuring principle of pre-magnetization measurement. In detail it can be proceeded such that the water fraction $\alpha_W$ and the hydrocarbon fraction $\alpha_C$, being the sum of the oil fraction $\alpha_O$ and the gaseous fraction $\alpha_G$, $\alpha_C=\alpha_O+\alpha_G$, are measured by means of electrical capacitance tomography and the water fraction and the hydrocarbon fraction are determined by the distribution of the permittivities or by the distribution of the conductivity of the medium, that the oil fraction $\alpha_O$ and the water fraction $\alpha_W$ are measured by means of measuring the pre-magnetization contrast, wherein the pre-magnetization contrast is realized by changing the length of the pre-magnetization section or by varying the measuring positions and that the gaseous fraction $\alpha_G$ is calculated by subtracting the oil fraction $\alpha_O$ measured by means of pre-magnetization contrast measurement from the hydrocarbon fraction $\alpha_C$ measured by electrical capacitance tomography, $\alpha_G=\alpha_{C,ECT}-\alpha_{O,VM}$.

It is also possible to proceed such that the water fraction $\alpha_W$ and the hydrocarbon fraction $\alpha_C$, being the sum of the oil fraction $\alpha_O$ and the gaseous fraction $\alpha_G$, $\alpha_C=\alpha_O+\alpha_3$, are measured by means of electrical capacitance tomography and the water fraction and the hydrocarbon fraction are determined by the distribution of the permittivities or by the distribution of the conductivity of the medium, that the ratio of the oil fraction $\alpha_O$ to the water fraction $\alpha_W$ is determined by means of pre-magnetization contrast measurement (OWR=$\alpha_O/\alpha_W$), wherein the pre-magnetization contrast is realized by changing the length of the pre-magnetization section or by varying the measuring positions and that first the oil fraction $\alpha_O$ is determined from the measured values by multiplying the water fraction $\alpha_W$ measured by means of electrical capacitance tomography with the OWR determined by means of pre-magnetization contrast measurement, $\alpha_O$=OWR·$\alpha_{W,ECT}$, and then the gaseous fraction $\alpha_G$ is determined by subtracting the calculated oil fraction from the hydrocarbon fraction $\alpha_C$ measured by means of electrical capacitance tomography, $\alpha_G$=$\alpha_{C,ECT}$ $\alpha_O$.

In the particular, realization of the method as described above, where the tomographic measuring principle is realized by electrical capacitance tomography and additionally the measuring principle of pre-magnetization measurement is implemented, it can supplementary be proceeded such that the mean conductivity of the medium is determined with the values measured by means of electrical capacitance tomography, that the additional load to the RF resonator circuit of the magnetic resonance tomograph due to the mean conductivity of the medium and/or at least one conducting phase of a multiphase medium is determined, and that the RF power fed in the medium for exciting the nuclear spins is enhanced such that the influence of the additional load due to the mean conductivity on the excitation of the nuclear spins is compensated.

In special this can supplementary be realized such that a conductivity map is generated over the cross sectional area of the measuring tube by means of electrical capacitance tomography, that the mean conductivity of the medium is calculated from the conductivity map, and that additionally the local deviations of the conductivity from the mean conductivity of the medium are determined with the conductivity map, that the additional load to the RF resonator circuit of the magnetic resonance tomograph due to the mean conductivity of the medium is determined, and that additionally the local damping of the RF field due to the local deviations of the conductivities from the mean conductivity are determined, and that the RF power fed in the medium for exciting the nuclear spins is enhanced such that the influence of the additional load due to the mean conductivity on the excitation of the nuclear spins is compensated and additionally RF power is fed locally in the medium, such that the influence of the local conductivities deviating from the mean conductivity on the excitation of the nuclear spins is compensated.

Finally, the method according to the invention, as it is described above, can be used for determining the salinity of the medium and/or at least one conducting phase of a multiphase medium by the conductivity of the medium and/or of at least one conducting phase of the multiphase medium.

In detail there are various possibilities for designing and further developing the flowmeter according to the invention. Here, reference is made to the following detailed description in conjunction with the accompanying drawings.

DETAILED DESCRIPTION OF THE INVENTION

All figures show a flowmeter 1 for determining the flow of a multiphase medium flowing through a measuring tube 2. All flowmeters 1 shown in the figures have in common, first of all, a first measuring device 3 and a second measuring device 4. At least one of the first and second measuring devices 3, 4 implements a tomographic measuring principle.

Figure 1:
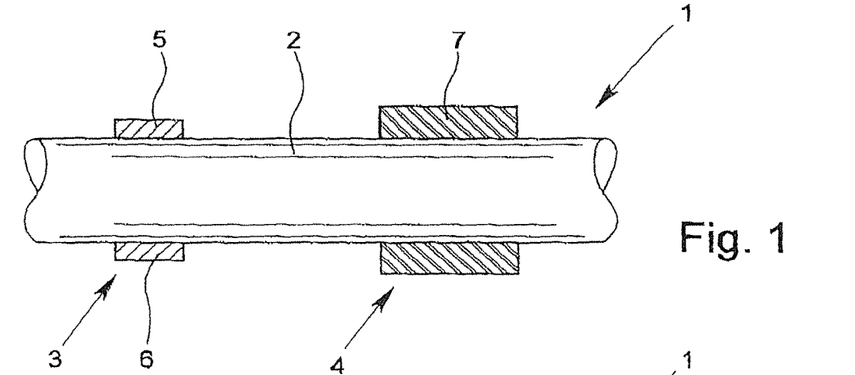
FIG. 1 shows a first embodiment of a flowmeter according to the invention implementing the measuring principle of magnetic resonance tomography and the measuring principle of electrical capacitance tomography.

In the embodiment of the flowmeter 1 according to the invention shown in FIG. 1, the first measuring device 1 is realized by an electrical capacitance tomograph. This electrical capacitance tomograph 5 has a number of electrodes 6 symmetrically arranged around the measuring tube 2. The electrical capacitance tomograph 5 is designed such that the electrodes are attachable to the outside to the measuring tube 2. This guarantees that the flow of the multiphase medium through the measuring tube 2 is not influenced or disturbed by the electrodes 6. The measuring signals arising at the electrodes 6 are evaluated by an evaluation unit (not shown here) and are constructed to a two dimensional permittivity distribution map of the cross-section area of the measuring tube 2 by a suitable algorithm.

The second measuring device 4 of the flowmeter 1 shown in FIG. 1 is realized by a magnetic resonance tomograph 7, which is also arranged around the measuring tube 2. The magnetic resonance tomograph 7 includes a unit for generating a constant magnetic field, (not shown), and also a unit for generating a gradient magnetic field G (not shown), that can be superimposed on the constant magnetic field, a exciting coil for generating a RF exciting pulse or a RF exciting pulse sequence (not shown) and also a detection coil (not shown), with which the measuring signal generated by the nuclear spins can be detected. The exciting coil and the detecting coil can be realized a single coil. It is possible to generate a gradient field g along the z-direction, $G=G_z \cdot e_z$ and/or a gradient field along the y-direction $G=G_y \cdot e_y$. This can be done simultaneously, $G=G_y \cdot e_y + G_z \cdot e_z$, as well as one after the other. The definition of the x-, y- and z-directions is indicated in the drawings below the FIG. 3 legend.

Figure 2:
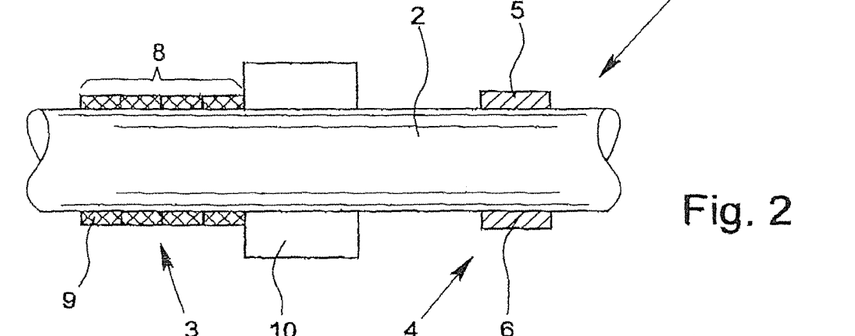
FIG. 2 shows a second embodiment of a flowmeter according to the invention implementing the measuring principle of electrical capacitance tomography and the measuring principle of pre-magnetization measurement.

For the embodiment according to FIG. 2, the first measuring device 3 is realized by a measuring device implementing the measuring principle of pre-magnetization contrast measurement, which shows a pre-magnetization section 8 with a constant magnetic field. The magnetic field has at least one component perpendicular to the direction of flow of the multiphase medium and is generated by magnetic field generating elements 9, which are arranged around the measuring tube 2. The section permeated by the magnetic field depends on the number of magnetic field generating elements 9 and the direction of the generated magnetic fields with respect to each other.

Also an assembly 10 for exciting the nuclear spins by a RF exciting pulse or a RF exciting pulse sequence and for measuring the measuring signals generated by the nuclear spins is part of the first measuring device 3.

Figure 4:
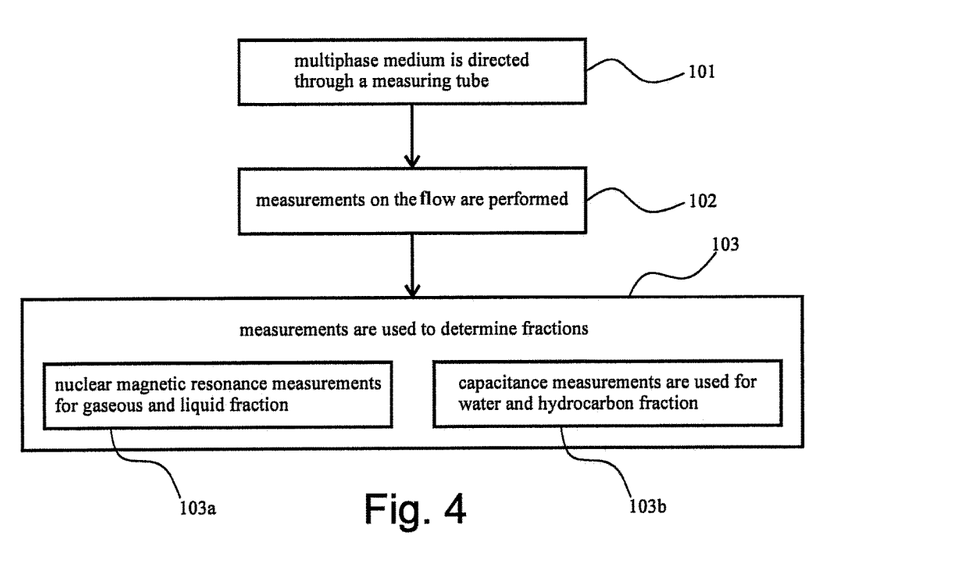
FIG. 4 shows a method for operating a flowmeter for determining the flow of a multiphase medium flowing through a measuring tube having two different types of measuring devices.

According to the embodiment of a flowmeter according to the invention shown in FIG. 4, the second measuring device 4 is realized by an electrical capacitance tomograph 5. This electrical capacitance tomograph 5 can be realized in the same manner and the same things can be achieved as was already mentioned in conjunction with the embodiment according to FIG. 1.

Figure 3:
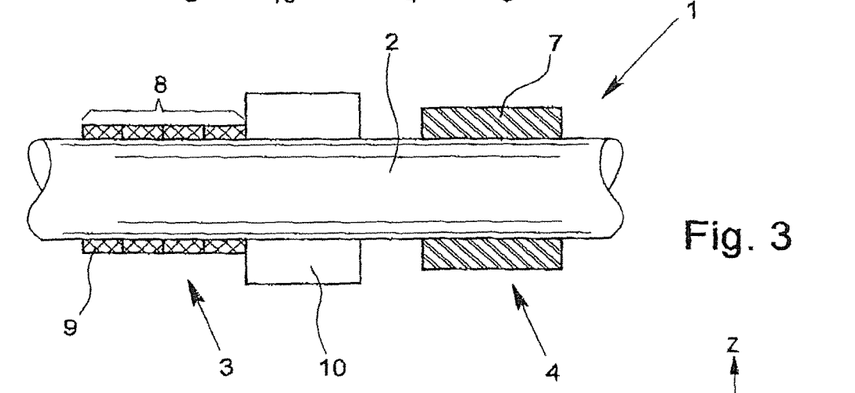
FIG. 3 shows a third embodiment of a flowmeter according to the invention implementing the measuring principle of magnetic resonance tomography and the measuring principle of pre-magnetization contrast measurement.

For the embodiment according to the invention shown in FIG. 3, what was already explained above is valid in that it contains a first measuring device 3 and a second measuring device 4. Here, the first measuring device 3 implements the measuring principle of pre-magnetization measurement and contains a pre-magnetization section 8, which is permeated by a constant magnetic field. Also here, the magnetic field is generated by a number of magnetic field generating elements 9, which are arranged around the measuring tube 2, and has at least one component perpendicular to the direction of flow of the multiphase medium. Also here, the measuring device 3 contains an assembly 10 for exciting the nuclear spins by a RF exciting pulse or a RF exciting pulse sequence and for measuring the measuring signals generated by the nuclear spins. The pre-magnetization 8 interfused by the effective magnetic field is defined and varied by the number of the magnetic field generating elements 9 and/or the direction of the magnetic fields generated by the magnetic field generating elements 9 with respect to each other.

For the schematically shown embodiment shown in FIG. 3, it is further valid that the tomographic measuring principle is realized by magnetic resonance tomography. Therefore, the embodiment contains a magnetic resonance tomograph 7. This magnetic resonance tomograph 7 can be realized in the same manner and the same results can be reached as was already mentioned in conjunction with the magnetic resonance tomograph 7 belonging to the embodiment according to FIG. 1.

FIG. 4 depicts a first method for operating a flowmeter for determining the flow of a multiphase medium flowing through a measuring tube. The method comprises the following steps:

In a first step 101, a flow of a multiphase medium is directed through a measuring tube having two different types of measuring devices.

In a second step 102, measurements on the flow are performed with the measuring devices, one of measurements being a nuclear magnetic resonance measurement and another of said measurements being an electrical capacitance measurement.

In a third step 103, said measurements are used to determine an amount of each of respective fractions of which the multiphase medium is comprised.

The third step 103 comprises two sub steps.

In a first sub-step 103*a*, the nuclear magnetic resonance measurement is used to determine a gaseous fraction and a liquid fraction of the medium by applying a gradient magnetic field along y and z axes relative to the measuring tube, an x axis being in a direction of flow through the measuring tube.

In a second sub-step 103*b*, the electrical capacitance measurement is used to determine a water fraction and a hydrocarbon fraction using a distribution of one of permittivities and conductivity of the medium.

Figure 5:
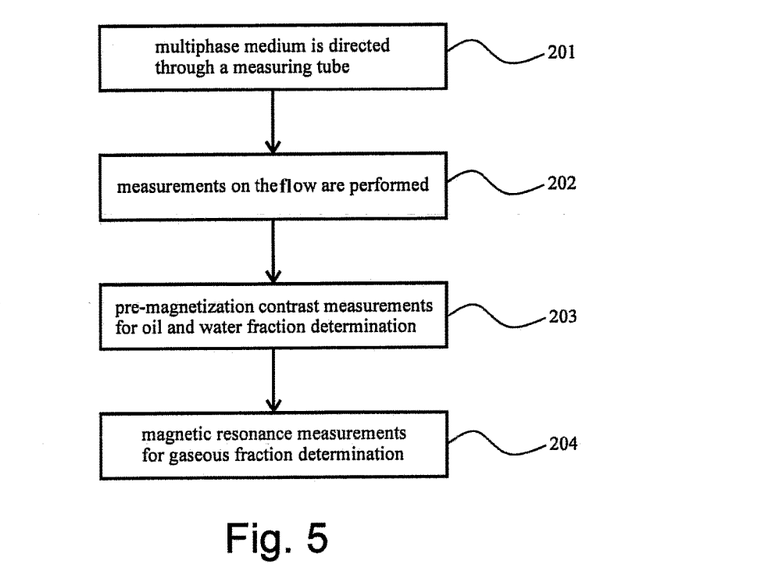
FIG. 5 depicts a second method for operating a flowmeter for determining the flow of a multiphase medium flowing through a measuring tube.

FIG. 5 depicts a second method for operating a flowmeter for determining the flow of a multiphase medium flowing through a measuring tube. The method comprises the following steps:

In a first step 201, a flow of a multiphase medium is directed through a measuring tube having two different types of measuring devices.

In a second step 202, measurements of the flow are performed with the measuring devices, one of measurements being a nuclear magnetic resonance measurement and another of said measurements being a pre-magnetization contrast measurement.

In a third step 203, the pre-magnetization contrast measurement is used to determine an oil fraction and a water fraction of the multiphase medium by one of changing a length of a pre-magnetization section or by varying measuring positions.

In a fourth step 204, the magnetic resonance measurement is used to determine a gaseous fraction by applying a gradient magnetic field along a z-axis and a y-axis, an x axis being in a direction of flow through the measuring tube.

Figure 6:
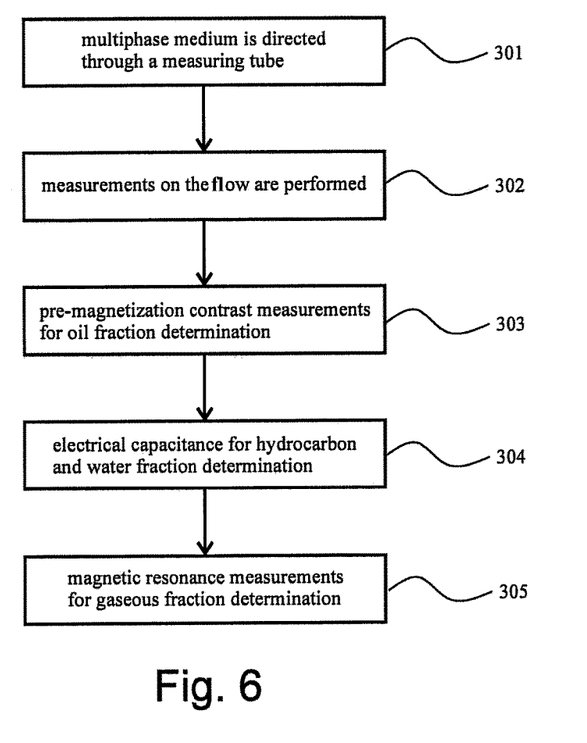
FIG. 6 depicts a third method for operating a flowmeter for determining the flow of a multiphase medium flowing through a measuring tube.

FIG. 6 depicts a third method for operating a flowmeter for determining the flow of a multiphase medium flowing through a measuring tube. The method comprises the following steps:

In a first step 301, a flow of a multiphase medium is directed through a measuring tube having two different types of measuring devices, In a second step 302, measurements of the flow are performed with the measuring devices, one of measurements being a nuclear magnetic resonance measurement and other of said measurements being a pre-magnetization contrast measurement and an electrical capacitance measurement.

In a third step 303, the pre-magnetization contrast measurement is used to determine an oil fraction of the multiphase medium by one of changing a length of a pre-magnetization section or by varying measuring positions.

In a fourth step 304, the electrical capacitance is used to determine a hydrocarbon fraction and a water fraction of the multiphase medium from a distribution of one of permittivities and conductivity of the medium.

In a fifth step 305, the magnetic resonance measurement is used to determine a gaseous fraction by applying a gradient magnetic field along a z-axis and a y-axis, an x axis being in a direction of flow through the measuring tube.

What is claimed is:

1. A method for operating a flowmeter for determining the flow of a multiphase medium flowing through a measuring tube, comprising: directing a flow of a multiphase medium through a measuring tube having two different types of measuring devices,     performing measurements on the flow with the measuring devices, one of measurements being a nuclear magnetic resonance measurement and another of said measurements being an electrical capacitance measurement, and     using said measurements to determine an amount of each of respective fractions of which the multiphase medium is comprised,     wherein the nuclear magnetic resonance measurement is used to determine a gaseous fraction and a liquid fraction of the medium by applying a gradient magnetic field along y and z axes relative to the measuring tube, an x axis being in a direction of flow through the measuring tube, and wherein said electrical capacitance measurement is used to determine a water fraction and a hydrocarbon fraction using a distribution of one of permittivities and conductivity of the medium.

* * * * *